United States Patent [19]
Kane et al.

[11] Patent Number: 5,147,342
[45] Date of Patent: Sep. 15, 1992

[54] SYSTEMS FOR COLLECTING URINE AND OTHER BODY FLUIDS

[76] Inventors: Patricia B. Kane, 4529 Hitching Post Trail, Rockford, Ill. 61101; June G. Halvorson, 4068 Caraway Ct., Loves Park, Ill. 61111

[21] Appl. No.: 616,428

[22] Filed: Nov. 21, 1990

[51] Int. Cl.[5] .................................. A61B 19/00
[52] U.S. Cl. .................................. 604/356; 220/737; 220/740
[58] Field of Search .................... D24/54; 232/41, 43; 604/356; 206/438, 569, 570; 220/212, 737, 738, 740; 215/100 A; 128/760

[56] References Cited

U.S. PATENT DOCUMENTS

| | | |
|---|---|---|
| D. 217,793 | 6/1970 | Hachmeister . |
| D. 258,311 | 2/1981 | Peterson . |
| D. 306,648 | 3/1990 | Jones et al. ............... D24/54 |
| 2,628,054 | 2/1953 | Fazakerley . |
| 3,335,714 | 8/1967 | Giesy . |
| 3,473,172 | 10/1969 | Friedman et al. . |
| 3,575,225 | 4/1971 | Muheim . |
| 3,625,654 | 12/1971 | Van Duyne . |
| 3,727,244 | 4/1973 | Collins . |
| 3,927,426 | 12/1975 | Geddes . |
| 4,687,129 | 8/1987 | Cugley ........................ 206/470 |
| 4,989,742 | 2/1991 | Powell ......................... 220/737 |

Primary Examiner—Randy C. Shay
Assistant Examiner—Gina Gualtieri
Attorney, Agent, or Firm—Fuller, Ryan, Hohenfeldt & Kees

[57] ABSTRACT

An assembly for handling a collection container for urine or another body fluid employs a generally rigid body with a holder end and a handle end. The holder end receives and supports the collection container in an upright position to receive the fluid. The handle end forms a structure for the user to hold the supported collection container in an outwardly extended position away from the user's hand. The handle structure also includes a cover for the container. After using the handle structure to position the container for collection of the fluid, the user can then use the cover as a lid to close the collection container. The body of the handle/holder can include a pre-weakened region along which the dual handle/cover can be separated from the holder to free the cover for use.

34 Claims, 4 Drawing Sheets

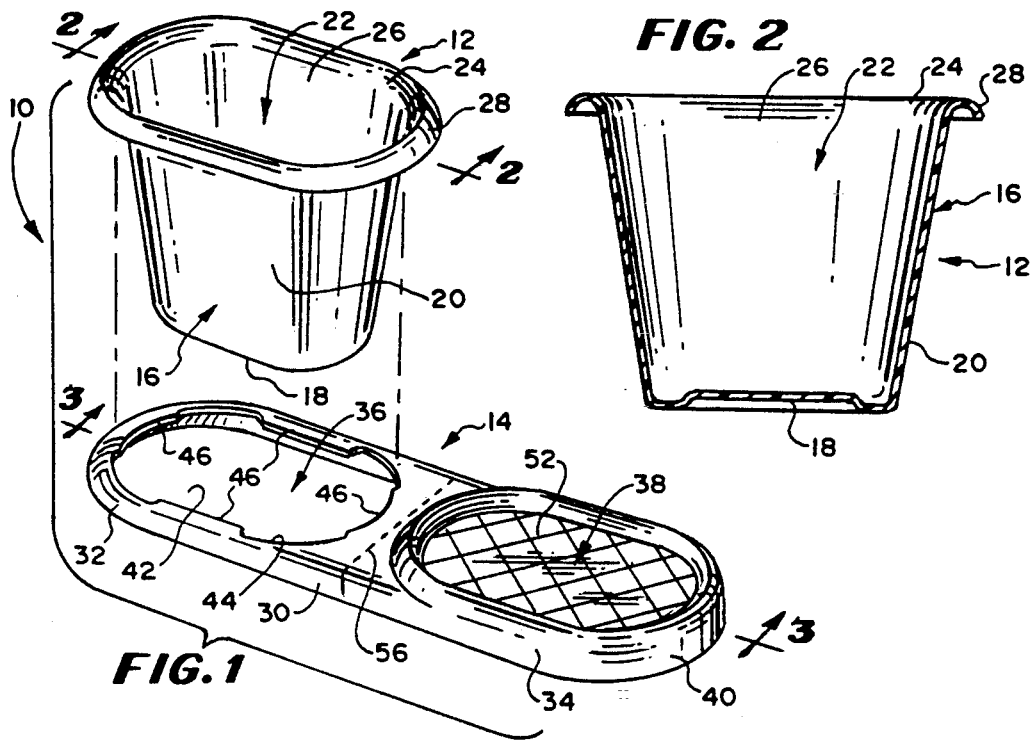
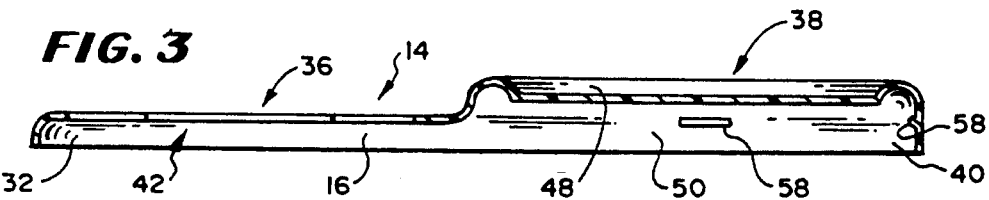
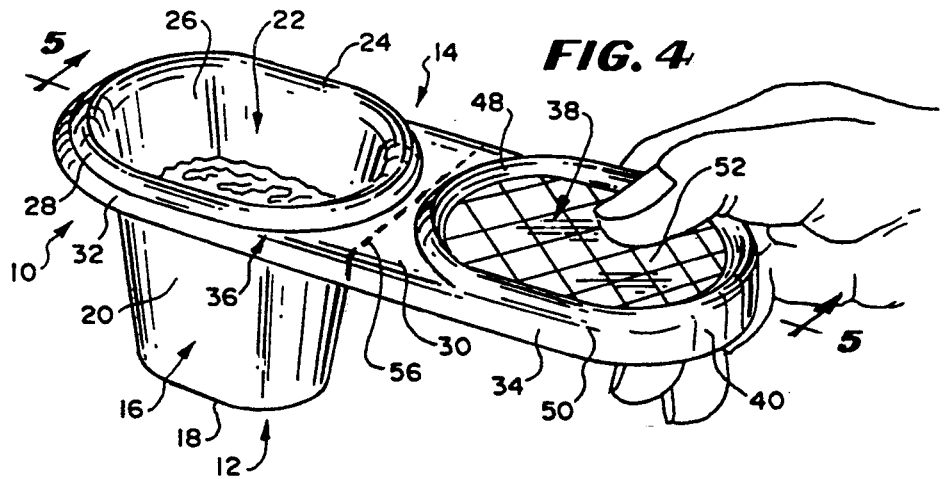

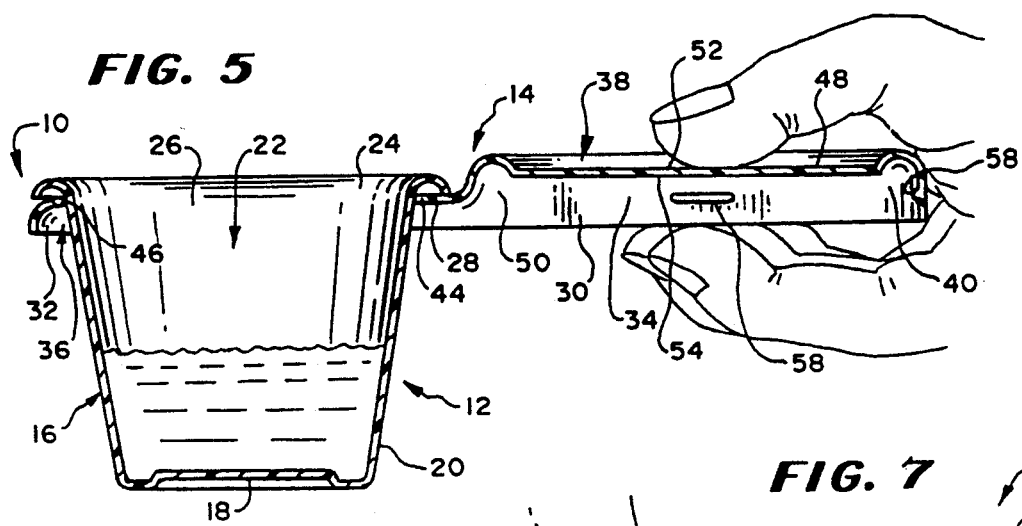
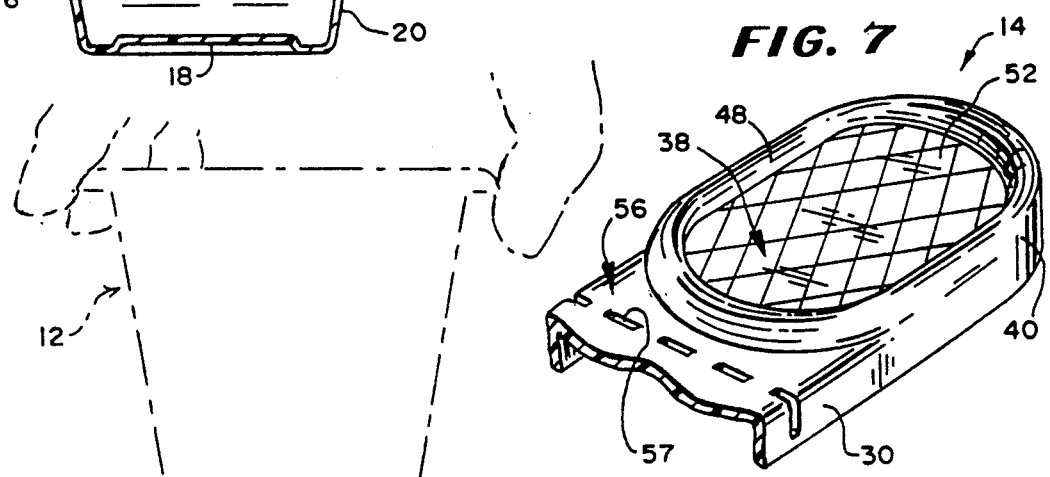
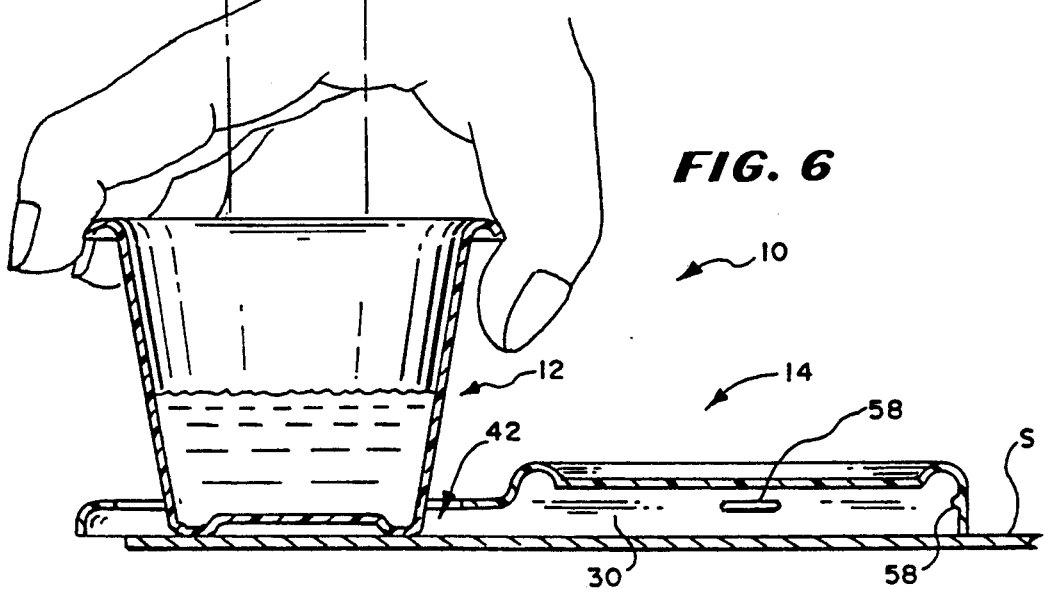

SYSTEMS FOR COLLECTING URINE AND OTHER BODY FLUIDS

FIELD OF THE INVENTION

Our invention relates to fluid collection systems and devices. In a more specific sense, our invention also relates to systems and devices for collecting body fluids like urine.

BACKGROUND OF THE INVENTION

Health professionals have for many years examined body fluids to assess a person's physical health and fitness. Urine is one body fluid that has been routinely collected for analysis by health professionals. Today, employers are also beginning to collect urine specimens from present and prospective employees to detect potential substance abuse and other health related problems that can affect job performance.

In collecting urine and other body fluids, it is important to obtain uncontaminated samples. Aseptic collection techniques are therefore required. It is also important that the collection devices are easy to use by men, women, and children. Balanced against these largely medical and physiological requirements is the importance of providing collection devices at a reasonable, low cost.

There are many devices and system specially designed for the collection of urine and other body fluids. The following patents represent prior attempts in these and related areas:

Fazakerly U.S. Pat. No. 2,628,054
Giesy U.S. Pat. No. 3,335,714
Friedman et al U.S. Pat. No. 3,473,172
Munheim U.S. Pat. No. 3,575,225
Duyne U.S. Pat. No. 3,625,654
Collins U.S. Pat. No. 3,727,244
Geddes U.S. Pat. No. 3,927,426
Peterson Des. 258,311

Our invention aims to provide an improved system for collecting a body fluid like urine that meets the demands of aseptic collection techniques, ease of use regardless of sex or age, and low cost.

SUMMARY OF THE INVENTION

To achieve this and other objectives, our invention provides new systems for collecting urine and other body fluids. The systems that embody our invention promote aseptic techniques without sacrificing ease of use by members of both sexes and all ages. The systems are low cost and disposable.

Our invention provides an assembly for handling a urine collection container in a straightforward and aseptic manner. The assembly includes a generally rigid body with oppositely spaced ends. One end of the body includes a holder for the collection container. The user places the collection container in the holder. The holder supports the collection container in an upright position to receive the intended fluid.

The other end of the body extends from the holder and forms a handle structure. By grasping this handle structure, users can hold the supported collection container in an outwardly extended position away from their hands. The handle structure simplifies use and promotes aseptic collection techniques.

The handle structure also forms an integral cover for the collection container. The handle structure therefore actually serves two purposes. After being used to position the collection container as the sample is collected, the same handle structure can be used to cover the collection container. The ready availability of the cover further promotes ease of use and aseptic techniques.

In a preferred embodiment, the body of the handling assembly includes a pre-weakened region between the holder and the dual purpose handle/cover structure. The user can break the body along this pre-weakened region to separate the handle/cover structure from the holder. This frees the cover for use as a lid for the collection container.

In a preferred embodiment, the collection container is itself specially designed to complement the features of the handling assembly. In one arrangement, a lip surrounds the opening through which fluid enters the container. The holder end of the handling assembly uses this lip as a point of support for the container. In this arrangement, the other end of the handling assembly includes a skirt that, when this end is used as a cover, overlies the lip to seal the container opening. The container lip therefore complements the functions of both the holder and the cover.

In another arrangement, the sidewall of the container tapers out toward the container opening. In this arrangement, the holder end of the handling assembly includes a cradle opening for receiving the container. Tabs extend into the cradle opening for engaging a region of the tapering sidewall of the container. The tapered shape of the container wedges against the support tabs to stabilize the container within the holder while fluid is collected. Afterward, the container can be easily separated from the holder, capped by the cover, and sent for analysis.

In another arrangement, the container opening is generally elliptical or elongated in shape. This special shape simplifies use of the container by women. The presence of a handle for holding the container away from the user also simplifies its use by women.

In another arrangement, the containers are shaped so that the body of one container can be nested within the fluid chamber of another container. This permits stacking of two or more containers for storage in a compact arrangement before use. Preferably in this arrangement, two or more handling elements also can be stacked one atop the other for storage in a compact cluster before use.

Other features and advantages of our invention will become apparent after considering the accompanying drawings, description, and claims.

DESCRIPTION OF THE DRAWINGS

FIG. 1 is an exploded perspective view of a system for collecting body fluids such as urine that embodies the features of our invention;

FIG. 2 is a side sectional view of the collection container associated with the system shown in FIG. 1, taken generally along line 2—2 in FIG. 1;

FIG. 3 is a side sectional view of the container handling assembly associated with the system shown in FIG. 1, taken generally along line 3—3 in FIG. 1;

FIG. 4 is a perspective view of the system shown in FIG. 1 in the hand of the user, with the collection container supported in an upright and outwardly extended position away from the user's hand;

FIG. 5 is a side section view of the system being used as shown in FIG. 4, taken generally along line 5—5 in FIG. 4;

FIG. 6 is side sectional view showing the sequence of removing the collection container from the handle structure;

FIG. 7 is an enlarged perspective view of the weakened area formed on the handling assembly, along which the handling assembly is broken by the user to separate the holder end from the handle end, the handle end then being free to serve as a lid for the collection container;

DESCRIPTION OF THE PREFERRED EMBODIMENTS

Figure 8:
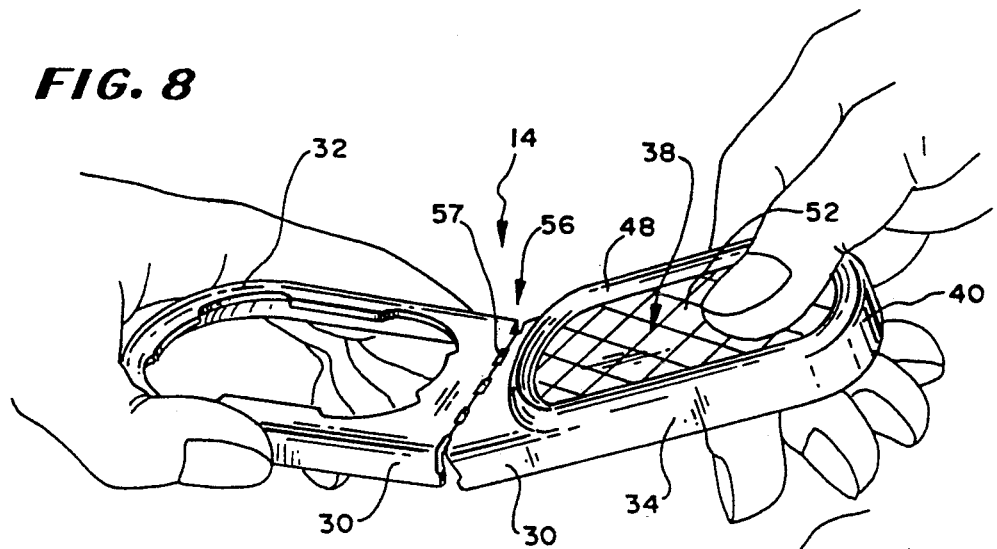
FIGS. 8 and 9 are perspective views showing the sequence of breaking the handling assembly to separate the holder end from the handle/lid end.

The drawings show a system 10 for collecting body fluids that embodies the features of our invention.

As there shown, the system 10 includes a collection container 12 for a body fluid. The system 10 also includes a separate assembly 14 for handling the collection container 12.

The system 10 is applicable for use in the collection of different types of body fluids. The system 10 shown in the illustrated embodiment collects urine samples. However, we do not intend to limit the use of our invention just to collecting urine.

The collection container 12 can itself be conventional in construction and shape. It can be made of either glass or plastic materials. Preferably, the container 12 is a single use, disposable component of relatively low cost. So, the container 12 is preferably made of an inert plastic material, such as polyethylene. Conventional injection or blow molding techniques can be used to make the container 12. As an alternative, the container 12 can be made of a fluid resistant paper or paper composite material that is inert and biodegradable.

In the illustrated embodiment, the container 12 includes certain structural features that complement the features and advantages of the associate handling assembly 14.

The container 12 includes a cup-shaped body 16 having a bottom wall 18 and an upstanding sidewall 20. The bottom wall 18 and sidewall 20 enclose an interior fluid chamber 22. The sidewall 20 terminates along an upper edge 24 forming an opening 26, through which fluids enter the chamber. An outwardly flared lip 28 extends from the upper sidewall edge 24.

As best shown in FIG. 2, the sidewall 20 tapers outward from the bottom wall 18. As best shown in FIG. 1, the sidewall 20 is also elongated along one radial direction to form a generally elliptical shape. The elongated shape of the container 12 allows women to more easily use it.

In the illustrated embodiment, the container 12 holds about four (4) fluid ounces. Still, the volume of the container 12 can vary, according to the intended use, up to eight (8) ounces or more.

The handling assembly 14 includes a generally rigid body 30 having oppositely spaced end portions 32 and 34. The term "generally rigid" means that the body 30 of the assembly 14 will not easily bend or break under the weight of the container 12 when filled with fluid and handled in the manner described in this application. The term "generally rigid" encompasses both inflexible and rigid materials. The term also encompasses materials that are semi-flexible or resilient, if they have the strength to support and handle the weight of the container 12 in the manner described in this application.

Like the container 12, the assembly 14 is preferably also a single use, disposable component of relatively low cost. So, the handling assembly 14 is also preferably made of an inert plastic material, such as polyethylene. Like the container 12, conventional injection or blow molding techniques can be used to make the handling assembly 14. As an alternative, the assembly 14, like the container 12, can be made of a fluid resistant paper or paper composite material that is inert and biodegradable.

The handling assembly 14 includes holder means 36 on one end portion 32. The holder means 36 receives the collection container 12 and supports the collection container 12 in an upright position to receive urine, or whatever the fluid intended for collection happens to be.

The handling assembly 14 also includes handle means 38 that extends from the holder means 36, terminating at the other end portion 34 of the body 30. The handle means 38 forms a structure for users to grasp in one hand (see FIG. 4). When in the hand of the user, the handle means 38 holds the collection container 12 that is supporting by the holder means 36 in an outwardly extended position away from the user's hand.

The handle means 38 also includes cover means 40. The cover means 40 forms an integral part of the structure of the handle means 38. Thus, when the handle means 38 is not being used to hold the collection container 12, the cover means 40 can be brought into engagement with the collection container 12 to serve as a lid (see FIGS. 10 and 11).

The particular structures of the holder means 36 and the handle means 38 can vary according to the shape and structure of the collection container 12. In the illustrated embodiment, the holder means 36 includes a cradle opening 42 for receiving the container 12, bottom wall 18 first.

The shape of the cradle opening 42 generally conforms to the shape of the associated container 12. In the illustrated embodiment, the cradle opening 42, like the container 12, is generally elongated in one radial direction. The cradle opening 42 is positioned upon the body end portion 32 so that its elongated dimension extends toward the handle means 38 at the other body end portion 34. So, when the container 12 is held in its upright position within the cradle opening 42, the elongated dimension of the container 12 also extends between the two end portions 32 and 34 of the handling assembly 14. This orientation simplifies use of the elongated container 12 by both men and women of all ages.

A peripheral support surface 44 laterally extends around the cradle opening 42. When the container 12 passes through the cradle opening 42, the lip 28 of the container 12 eventually engages the lateral support surface 44. The engagement between the lip 28 and the support surface 44 suspends the container 12 in the upright position within the cradle opening 42 (see FIG. 5).

Also in the illustrated embodiment, portions of the lateral support surface 44 extend into the cradle opening 42 to form a series of arcuately spaced tabs 46. As the lip 28 contacts the support surface 44, the tabs 46 also bear against a region of the tapering sidewall 20 near the container lip 28.

The illustrated arrangement wedges the tapering container sidewall 20 against the tabs 46. The tabs 46 stabilize the container 12 in its upright position within the cradle opening 42. The arrangement also allows easy removal of the container 12 from the cradle opening 42 after collection of the fluid sample. As FIG. 6 shows, after collecting a fluid sample, the user can lower the container 12 onto a flat surface S. With the container 12 resting on the flat surface S, the user can slip the handling assembly 14 down upon the surface S, and lift the container 12 free of the cradle opening 42 (as shown in phantom lines in FIG. 6).

In the illustrated embodiment, the structure of the cover means 40 includes a lid portion 48 and a skirt portion 50. The lid portion 48 includes a top surface 52 and a bottom surface 54. When the handle means 38 holds the container 12 in the outwardly extended position (as FIG. 4 shows), the top surface 52 of the lid portion 48 generally faces upward. When in this mode of use, the bottom surface 54 of the lid portion 48 generally faces downward.

Figure 10:
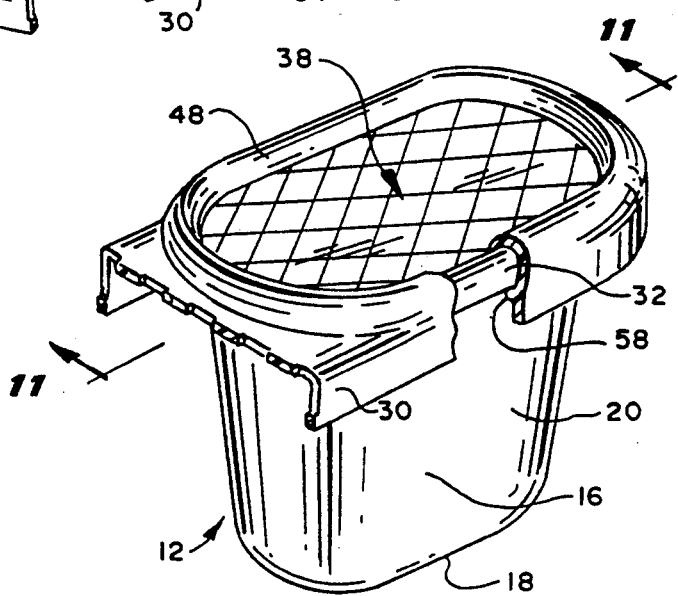
FIG. 10 is a perspective view of the collection container covered with the dual purpose handle structure of the handling assembly after the collection of the fluid sample.
Figure 11:
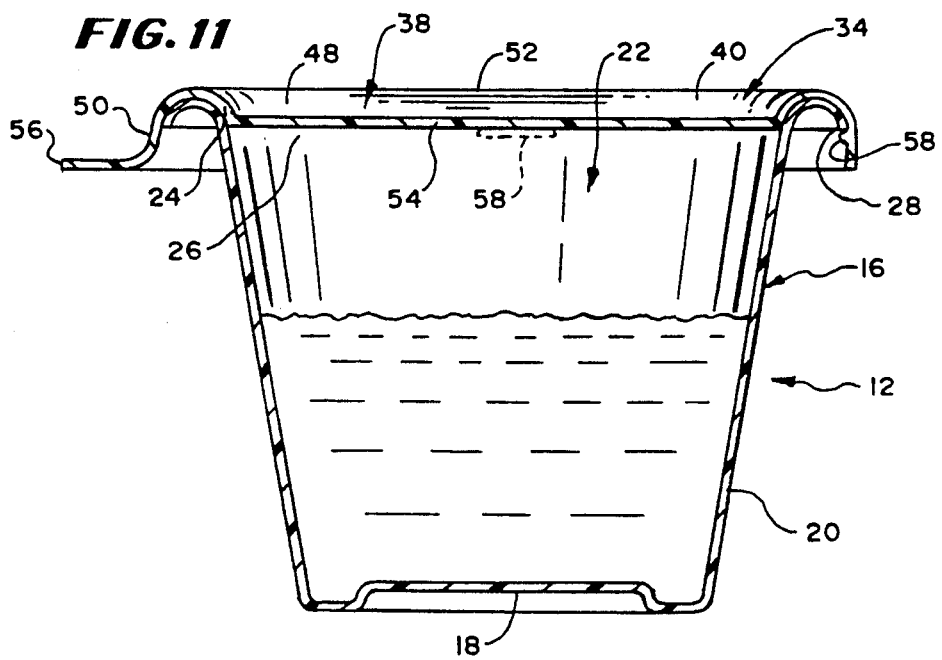
FIG. 11 is a side section view of the collection container covered with the dual purpose handle structure of the handling assembly taken generally along line 11—11 in FIG. 10.

When the cover means 40 engages the opening 26 of the container 12, the lid portion 48 overlies the opening 26, while the skirt portion 50 overlies the lip 28 of the container 12 (see FIGS. 10 and 11). When in this position, the bottom surface 54 of the lid portion 48 faces the interior of the fluid chamber 22, while the top surface 52 is exposed to the exterior.

In the illustrated and preferred embodiment, one or more tabs 58 extend out from the interior of the skirt portion 50 (see FIGS. 3, 5 and 6). When the lid portion 48 overlies the opening 26, the tabs 58 abut against the underportion of the container lip 28 (as best shown in FIG. 10). The tabs 58 make a snap-fit engagement with the lip 58 to secure the cover means 40 in place upon the container 12.

To better help the user make use of the dual purpose handle/cover structure of the handling assembly 14, the body 30 includes a pre-weakened area 56 between the holder means 36 and the handle means 38. The pre-weakened area 56 is formed during the molding process. The area 56 can take the form of a series of preformed openings 57 (see FIG. 7) that weaken the structure of the body 30. The area 56 also can take the form of a thinned area that also weakens the structure of the body 30.

Figure 9:
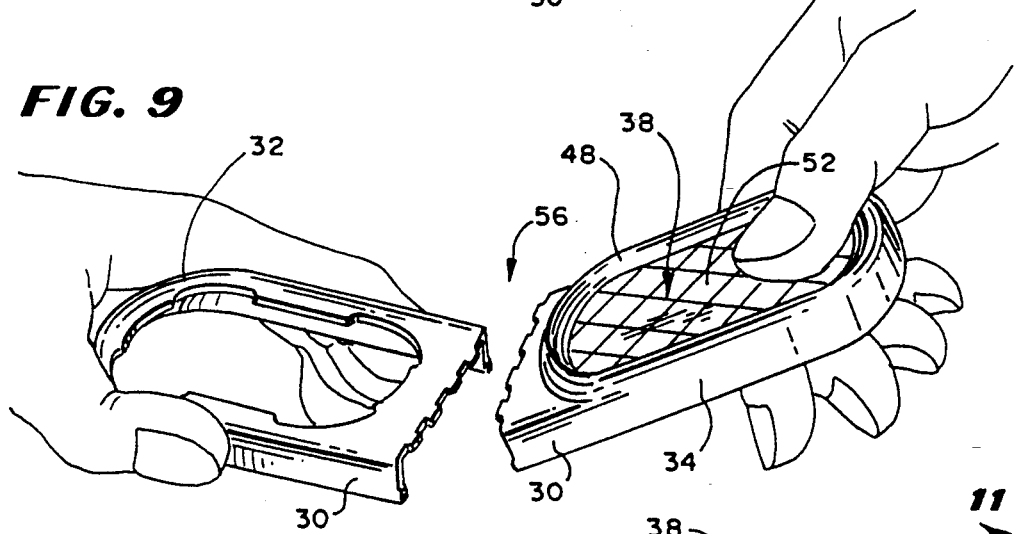

After collecting the fluid sample within the container 12, the user can apply force to bend the body 30 of the handling assembly 14 along the weakened area 56 (as FIGS. 8 and 9 show). Flex bending will break the body 30 along the weakened area 56. The user can then separate the end 34 of the body 30 having dual purpose handle/cover from the end 32 of the body 30 having the holder means 36. This frees the cover means 40 for use as a lid for the collection container 12.

Alternatively, the user could cut the body 30 of the handling assembly 14 with scissors, with or without the presence of the weakened area 56.

Figure 12:
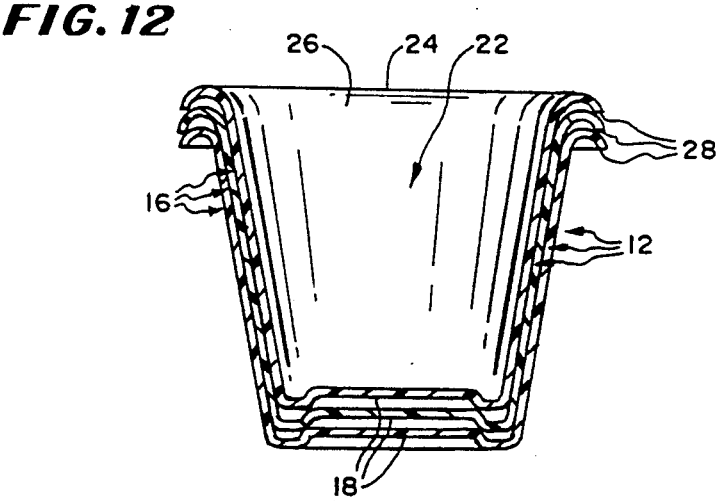
FIG. 12 is a side section view of several collection containers nested one within the other for storage prior to use.

In the illustrated embodiment (as FIG. 12 shows), the body of one container 12 can be nested within the fluid chamber 22 of another container 12. This allows two or more containers 12 to be conveniently stacked in a compact grouping for storage before use.

Figure 13:
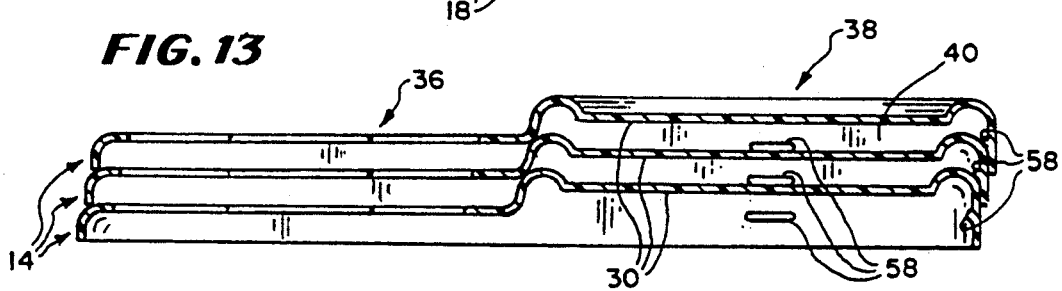
FIG. 13 is a side section view of several handling elements stacked one atop the other for storage prior to use.

Also (as FIG. 13 shows), the shape of the handling assembly 14 allows two or more of them to be nested in a compact stack. A supply of handling assemblies also can be stored conveniently one atop the other prior to use.

The following claims set forth the features and advantages of our invention.

We claim:

1. A system for collecting body fluids comprising:
a first unitary component part comprising a container having a chamber with an opening for receiving fluid, and
a second unitary component part comprising a handling assembly for the container comprising
holder means for removably receiving the container and supporting the container in an upright position to receive fluid through the opening, and
handle means extending from the holder means and forming a generally rigid structure for the user to support the container, when it is removably received by the holder means, in an outwardly extended position away from the user's hand, the handle means including cover means of substantially the same size as said chamber opening and being operative, when the container is removed from the holder means for movement into engagement with the opening of the container.

2. A system according to claim 1
wherein the handling assembly includes a body with oppositely spaced end portions, and
wherein the holder means is located on one end portion and the structure of the handle means extends from the holder means to the other end portion.

3. A system according to claim 2
wherein the handling means includes means located on the body between the holder means and the handle means for defining a pre-weakened region along which the handle means can be separated from the holder means to free the cover means for engagement with the opening of the container.

4. A system according to claim 1
wherein the container includes a lip that surrounds the opening, and
wherein the holder means includes a surface that contacts the container lip for supporting the container in the fluid-receiving position.

5. A system according to claim 4
wherein the cover means includes a skirt portion that overlies the container lip when the cover means engages the opening.

6. A system according to claim 1
wherein the container includes a lip that surrounds the opening, and
wherein the cover means includes a lid portion that overlies the opening and a skirt portion that overlies the container lip.

7. A system according to claim 6
wherein the lid portion includes a top surface and a bottom surface, wherein, when the structure of the handle means is being used to hold the container in the outwardly extended position, the top surface of the lid portion generally faces upward and the bottom surface of the lid portion generally faces downward, and wherein, when the cover means engages the opening of the container, the bottom surface of the lid portion faces the interior of the fluid chamber.

8. A system according to claim 1 wherein the opening of the container is generally elliptical in shape.

9. A system according to claim 1
wherein the opening of the container is generally elongated in one radial direction,
wherein, when the container is received and supported by the holder means in its fluid-receiving position, the elongated radial direction of the container extends toward the handle means of the container handling assembly.

10. A system according to claim 1
wherein the holder means includes a cradle opening for receiving the container, the cradle opening including contact means for engaging the container to support the container in the upright position within the cradle opening.

11. A system according to claim 10
wherein the container includes a lip surrounding its opening, and
wherein the contact means includes a support surface for engaging the lip to support the container within the cradle opening.

12. A system according to claim 10
wherein the container includes a sidewall that tapers outwardly toward the opening, and
wherein the contact means includes tab means extending into the cradle opening for engaging a region of the tapering sidewall of the container.

13. A system according to claim 12
wherein the container includes a lip surrounding the opening, and
wherein the contact means includes a support surface for engaging the lip to support the container within the cradle opening.

14. A system according to claim 1
wherein one container can be nested within the fluid chamber of another container to permit stacking of two or more containers for storage.

15. A system according to claim 1
wherein two or more handling assemblies can be stacked for storage one atop the other.

16. An assembly for handling a urine collection container comprising
a generally rigid body having oppositely spaced end portions,
holder means on one end portion for removably receiving the collection container and supporting the collection container in an upright position to receive urine, and
handle means extending from the holder means and terminating at the other end portion forming a structure for the user to support the collection container, when it is removably received by the holder means, in an outwardly extended position away from the user's hand, the handle means including cover means operative, when the collection container is removed from the holder means, for movement into closely surrounding engagement with the collection container to serve as a lid.

17. An assembly for handling a urine collection container comprising
a generally rigid body having oppositely spaced end portions,
holder means on one end portion for removably receiving the collection container and supporting the collection container in an upright position to receive urine,
handle means extending from the holder means and terminating at the other end portion forming a structure for the useer to support the collection container, when it is removably received by the holder means, in an outwardly extended position away from the user's hand, the handle means including cover means operative, when the collection container is removed from the holder means, for movement into engagement with the collection container to serve as a lid, and
means located on the body between the holder means and the handle means for defining a pre-weakened region along which the handle means can be separated from the holder means to free the cover means for use as a lid for the collection container.

18. A system for collecting body fluids comprising:
a container having a chamber with an opening for receiving fluid, the container including a lip that surrounds the opening, and
a handling assembly for the container comprising
holder means for receiving the container and supporting the container in an upright position to receive fluid through the opening, and
handle means extending from the holder means and forming a generally rigid structure for the user to hold the container supported by the holder means in an outwardly extended position away from the user's hand, the handle means including cover means having a skirt portion and a lid portion with a top surface and a bottom surface that face, respectively, generally upward and downward when the structure of the handle means is being used to hold the container in the outwardly extended position, the cover means being operative, when the structure is not being used to hold the container in the outwardly extended position, for movement into engagement with the opening of the container with the lid portion overlying the opening with the bottom surface of the lid portion facing the interior of the fluid chamber and the skirt portion being closely adjacent to and overlying the container lip.

19. A system according to claim 18
wherein the handling assembly includes a body with oppositely spaced end portions, and
wherein the holder means is located on one end portion and the structure of the handle means extends from the holder means to the other end portion.

20. A system according to claim 19
wherein the handling means includes means located on the body between the holder means and the handle means for defining a pre-weakened region along which the handle means can be separated from the holder means to free the cover means for engagement with the opening of the container.

21. A system according to claim 18
wherein the opening of the container is generally elliptical in shape.

22. A system according to claim 18 wherein the opening of the container is generally elongated in one radial direction, wherein, when the container is received and supported by the holder means in its fluid-receiving position, the elongated radial direction of the container extends toward the handle means of the container handling assembly.

23. A system according to claim 18 wherein the holder means includes a cradle opening for receiving the container, the cradle opening including contact means for engaging the container to support the container in the upright position within the cradle opening.

24. A system for collecting body fluids comprising:
a container having a chamber with an opening for receiving fluid, and
a handling assembly for the container comprising
holder means including a cradle opening for receiving the container and having contact means for engaging the container within the cradle opening to support the container in an upright position therein to receive fluid through the container opening, and
handle means extending from the holder means and forming a generally rigid structure for the user to hold the container supported by the holder means in an outwardly extended position away from the user's hand, the handle means including cover means of substantially the same size as the chamber opening and being operative, when the structure is not being used to hold the container in the outwardly extended position, for movement into engagement with the opening of the container.

25. A system according to claim 24
wherein the container includes a lip surrounding its opening, and
wherein the contact means includes a support surface for engaging the lip to support the container within the cradle opening.

26. A system according to claim 24
wherein the container includes a sidewall that tapers outwardly toward the opening, and
wherein the contact means includes tab means extending into the cradle opening for engaging a region of the tapering sidewall of the container.

27. A system according to claim 26
wherein the container includes a lip surrounding the opening, and
wherein the contact means includes a support surface for engaging the lip to support the container within the cradle opening.

28. A system according to claim 24
wherein the handling means includes means located on the body between the holder means and the handle means for defining a pre-weakened region along which the handle means can be separated from the holder means to free the cover means for engagement with the opening of the container.

29. A system according to claim 24
wherein the container includes a lip that surrounds the opening, and
wherein the cover means includes a lid portion that overlies the opening and a skirt portion that overlies the container lip.

30. A system according to claim 29
wherein the lid portion includes a top surface and a bottom surface,
wherein, when the structure of the handle means is being used to hold the container in the outwardly extended position, the top surface of the lid portion generally faces upward and the bottom surface of the lid portion generally faces downward, and
wherein, when the cover means engages the opening of the container, the bottom surface of the lid portion faces the interior of the fluid chamber.

31. A system according to claim 24
wherein the opening of the container is generally elliptical in shape.

32. A system according to claim 24
wherein the opening of the container is generally elongated in one radial direction,
wherein, when the container is received and supported by the holder means in its fluid-receiving position, the elongated radial direction of the container extends toward the handle means of the container handling assembly.

33. A system according to claim 24
wherein one container can be nested within the fluid chamber of another container to permit stacking of two or more containers for storage.

34. A system according to claim 24
wherein two or more handling assemblies can be stacked for storage one atop the other.

* * * * *